(12) United States Patent
Broman et al.

(10) Patent No.: US 10,028,916 B2
(45) Date of Patent: Jul. 24, 2018

(54) ORALLY DISINTEGRATING DOSAGE FORM FOR ADMINISTRATION OF AVANAFIL, AND ASSOCIATED METHODS OF MANUFACTURE AND USE

(71) Applicant: Vivus, Inc., Mountain View, CA (US)

(72) Inventors: Calvin Theodore Broman, Saratoga, CA (US); Eric Sheu, Mountain View, CA (US)

(73) Assignee: Vivus, Inc., Campbell, CA (US)

( * ) Notice: Subject to any disclaimer, the term of this patent is extended or adjusted under 35 U.S.C. 154(b) by 0 days.

(21) Appl. No.: 14/714,028

(22) Filed: May 15, 2015

(65) Prior Publication Data

US 2016/0331687 A1    Nov. 17, 2016

Related U.S. Application Data

(60) Provisional application No. 61/994,349, filed on May 16, 2014.

(51) Int. Cl.
*A61K 31/506* (2006.01)
*A61K 9/20* (2006.01)
*A61K 9/00* (2006.01)

(52) U.S. Cl.
CPC .......... *A61K 9/2031* (2013.01); *A61K 9/0056* (2013.01); *A61K 9/2018* (2013.01); *A61K 9/2095* (2013.01); *A61K 31/506* (2013.01)

(58) Field of Classification Search
CPC .. A61K 9/2031; A61K 9/0056; A61K 9/2018; A61K 9/2095; A61K 31/506
See application file for complete search history.

(56) References Cited

U.S. PATENT DOCUMENTS

| 7,390,503 B1 * | 6/2008 | Ahmed | A61K 9/0056 424/464 |
| 2011/0229570 A1 * | 9/2011 | Sugimoto | A61K 9/0056 424/465 |

FOREIGN PATENT DOCUMENTS

| DE | 102005009241 | 2/2006 |
| EP | 1120120 A1 | 8/2001 |
| EP | 2698145 A1 | 2/2014 |
| WO | WO 2003072084 A1 | 9/2003 |
| WO | WO 2006092222 A1 | 9/2006 |
| WO | WO 2013019056 A1 | 2/2013 |

* cited by examiner

*Primary Examiner* — Sahar Javanmard
(74) *Attorney, Agent, or Firm* — Cooley LLP; Ivor R. Elrifi; Matthew Pavao

(57) ABSTRACT

Formulations are provided for the oral administration of avanafil, a Type V phosphodiesterase inhibitor ("PDE V inhibitor"), and analogs thereof. The formulations are orally disintegrating tablets (ODTs) that rapidly dissolve or disintegrate in the oral cavity. The tablets contain an absorption enhancing composition that increases the duodenal absorption of the active agent, following transfer from the low pH environment of the stomach to the more basic pH of the duodenum. Methods for administering the active agent using the dosage forms are provided. The invention also encompasses a method of selecting components and compositions to incorporate in the formulations which will facilitate increased absorption of the active agent in the duodenum and thus serve as "absorption enhancing compositions" herein. Also provided are methods for manufacturing orally disintegrating tablets to optimize the physical properties of the dosage forms, particularly hardness and disintegration time.

13 Claims, 4 Drawing Sheets

ORALLY DISINTEGRATING DOSAGE FORM FOR ADMINISTRATION OF AVANAFIL, AND ASSOCIATED METHODS OF MANUFACTURE AND USE

CROSS REFERENCE TO RELATED APPLICATIONS

This application claims priority to, and the benefit of, U.S. Provisional Patent Application Ser. No. 61/994,349 filed May 16, 2014, the contents of which are herein incorporated by reference in their entirety.

FIELD OF INVENTION

This invention relates generally to the field of drug delivery, and more particularly relates to an orally disintegrating dosage form for the administration and rapid absorption of a Type V phosphodiesterase inhibitor such as the N-heterocyclic-substituted ketone avanafil. The invention additionally relates to a method for manufacturing orally disintegrating dosage forms, and to a method for selecting compounds and compositions that enhance the absorption of basic active agents. The invention has utility in the fields of medicine and pharmaceutical formulation.

BACKGROUND OF THE INVENTION

In general, it is known that cyclic guanosine monophosphate ("cGMP"), which is an intracellular secondary messenger, is decomposed and inactivated by cyclic nucleotide phosphodiesterases ("PDEs") that hydrolyze cGMP into 5'-GMP. Such phosphodiesterases are widely distributed in many cell types and tissues of the living body. When PDE activity is inactivated by a an inhibitor of a cGMP-degrading phosphodiesterase, the level of cGMP in cells is increased, in turn triggering several physiological responses, including relaxation of vascular smooth muscle, relaxation of bronchial smooth muscle, and inhibition of platelet aggregation.

Moreover, it has been reported that certain cGMP-specific PDE inhibitors (i.e., inhibitors of phosphodiesterase Type V, or "PDE V inhibitors") are useful in the treatment of diseases caused by a functional disorder of cGMP signaling, including hypertension, angina pectoris, myocardial infarction, chronic or acute heart failure, pulmonary hypertension, etc. (see, e.g., International Patent Publication No. WO 96/05176), and prostatic hyperplasia (see Australian Patent Publication No. 9955977). It has also been reported that PDE V inhibitors can be useful in the treatment of female sexual dysfunction (see, e.g., U.S. Pat. No. 6,469,016 to Place et al., of common assignment herewith to Vivus, Inc.; and Vemulapalli et al. (2000) Life Sciences 67: 23-29), diabetic gastroparesis (Watkins et al. (2000) J. Clin. Invest. 106: 373-384), achalasia (Bortolotti et al. (2000) Gastroenterology 118: 253-257), diarrhea (Mule et al. (1999) Br. J. Pharmacol. 127: 514-520), constipation (Bakre et al. (2000) J. Cell. Biochem. 77: 159-167) and asthma (Turner et al. (1994) Br. J. Pharmacol. 111: 1198-1204).

Furthermore, sildenafil, 1-[4-ethoxy-3-(6,7-dihydro-1-methyl-7-oxo-3-propyl-1H-pyrazolo[4,3-d]pyrimidin-5-yl)-phenylsulfonyl]-4-methylpiperazine citrate, a cGMP-specific PDE V inhibitor, is now widely prescribed for the treatment of penile erectile dysfunction (as Viagra®, Pfizer), as are the cGMP-specific PDE V inhibitors tadalafil (as Cialis®, Lilly ICOS), and vardenafil (as Levitra®, Bayer AG). However, these PDE V inhibitors have been reported to have side effects such as headache, facial suffusion, gut disorder, rhinitis, color sense disorder, penile erectile continuance, back pain, abdominal pain, and nausea (see, e.g., Irwin et al. (1998) The New England Journal of Medicine 338(20):1397-1404; Morales et al. (1998) International Journal of Impotence Research 10(2): 69-73; and Goldenberg (1998) Clinical Therapeutics 20(6): 1033-1048). It has also been reported that the side effects of sildenafil affect vision, including blurriness and loss of peripheral vision.

In U.S. Pat. No. 6,656,935 to Yamada et al. (Tanabe Seiyaku Co. Ltd., Osaka, JP), the synthesis of a new class of cGMP-specific PDE inhibitors is described. These compounds are N-heterocyclic-substituted compounds having the general structure (I)

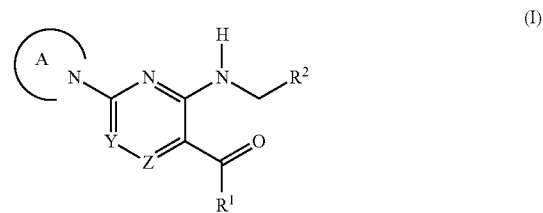

wherein: Ring A is a substituted or unsubstituted nitrogen-containing heterocyclic group; $R^1$ is a substituted or unsubstituted lower alkyl group, a substituent having the formula —NH-Q-$R^3$ wherein Q is a lower alkylene group or a single bond and $R^3$ is a substituted or unsubstituted nitrogen-containing heterocyclic group, or a substituent having the formula —NH—$R^4$ wherein $R^4$ is substituted or unsubstituted cycloalkyl; $R^2$ is substituted or unsubstituted aryl; and one of Y and Z is =CH— and the other is =N—, and also include pharmaceutically acceptable salts of the compounds. These compounds, particularly 4-[(3-chloro-4-methoxybenzyl)amino]-2-[2-(hydroxymethyl)-1-pyrrolidinyl]-N-(2-pyrimidinylmethyl)-5-pyrimidinecarboxamide, or "avanafil," having the structure

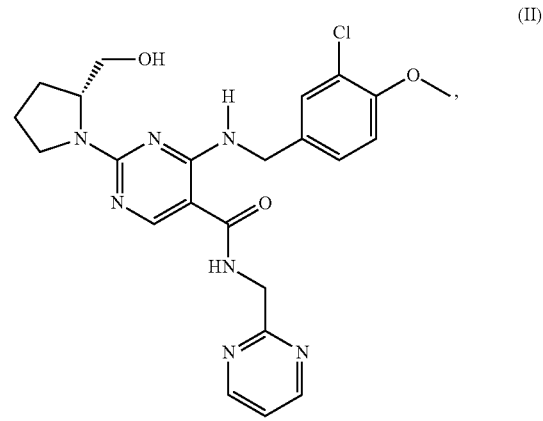 [SMILES: COc1ccc(CNc2nc(N3CCC[C@@H]3CO)ncc2C(=O)NCc2ncccn2)cc1Cl]

are particularly useful in the prophylaxis or treatment of erectile dysfunction with few side effects.

Administration of these therapeutic agents for the treatment of erectile dysfunction is generally on an as-needed basis rather than as part of an ongoing dosage regimen. It is also desirable that any erectile dysfunction pharmacotherapy be fast acting, so that a minimum of scheduling or advance planning is required prior to sexual activity. Although "immediate release" or "rapid release" dosage forms, including orally disintegrating tablets, have been known in the art for some time, various factors can significantly reduce the absorption of drugs from such tablets. For instance, certain drugs such as avanafil and its analogs are soluble in aqueous media at a low pH, but at elevated pH, such as that of the duodenum, the drug can precipitate quickly upon leaving the stomach and entering the duodenum, significantly reducing the likelihood of rapid absorption. If one could maintain a low enough local pH for the drug to remain in a dissolved state, absorption would not be a problem; there is difficulty, however, in maintaining a local low pH in the duodenum.

SUMMARY OF THE INVENTION

The present invention is directed to the aforementioned need in the art and provides an oral dosage form that provides for rapid absorption of avanafil or an analog thereof. Rather than attempting to maintain a locally lower pH as the drug enters the duodenum, i.e., in order to preclude quick precipitation and aggregation as discussed above, the invention involves formulating the dosage form to include means for reducing precipitation and aggregation as the drug is released from the stomach and enters the duodenum. The invention makes use of increased surface area, which, in part, increases absorption rate, and also incorporates into the dosage form at least one component that reduces precipitation and aggregation of the drug in the duodenum. By "reducing precipitation and aggregation" is meant: delaying the onset of precipitation; delaying the onset of aggregation; reducing the rate at which precipitation occurs; and/or reducing the rate at which aggregation occurs. An objective measure by which reduction of precipitation and aggregation may be evaluated is described in Example 2, in which various avanafil formulations are initially dissolved in water at a pH of 2.5, the pH of the solution is raised to 7.0, and light transmission as a function of time is recorded. Reduction of precipitation and aggregation may be defined accordingly as occurring when a composition displays less than a 60% reduction in transmission at after ten minutes at the elevated pH; this is equivalent to an asymptotic transmission of 60% at ten minutes following the upward adjustment of pH.

In a first embodiment, then, the invention provides an orally administrable formulation comprising a therapeutically effective amount of avanafil, a means for reducing precipitation and aggregation of the formulation as drug is released from the stomach and enters the duodenum, and a pharmaceutically acceptable carrier, wherein the means for reducing precipitation and aggregation comprises an absorption enhancing composition.

In another embodiment, the invention provides a method for administering a PDE V inhibitor to a subject by orally administering to the subject a formulation or dosage form as provided herein. Administration is generally not carried out within the context of an ongoing, regular (e.g., daily) dosage regimen, but rather may be and preferably is conducted on an as-needed basis, since the preferred formulations herein are orally disintegrating dosage forms that provide for rapid release and a short time to achieve an effective blood level of the active agent. When indicated for erectile dysfunction, then, administration of such dosage forms can be immediately prior to sexual activity, generally about fifteen minutes to about three hours prior to sexual activity, an advantage of the invention that eliminates the awkwardness and inconvenience of scheduling or otherwise planning sexual activity. Avanafil, a PDE V inhibitor, is also administered using the method of the invention to prevent or treat other disorders, adverse conditions, and diseases that are responsive to administration of a PDE V inhibitor, including, but not limited to, hypertension, angina pectoris, myocardial infarction, heart failure, pulmonary hypertension, prostatic hyperplasia, female sexual dysfunction, neurogenesis, neuropathy, Alzheimer's disease, psoriasis, skin necrosis, metastasis, baldness, nutcracker esophagus, anal fissure, hemorrhoids, insulin resistance syndrome, hypoxic vasoconstriction, and blood pressure stabilization.

The invention also provides a method for manufacturing an orally disintegrating dosage form having the desired characteristics discussed herein. In one embodiment, the method comprises a wet granulation technique involving an initial step in which a fraction, i.e., some but not all, of the formulation used to prepare the dosage form, is mixed, granulated and dried, a second step in which the remainder of the formulation is blended in, and, finally, compaction to prepare the rapidly disintegrating oral dosage form. Generally, the first fraction of the formulation contains active agent, water or an alternative solvent, preferably an aqueous solvent, a porous binder, and a disintegrant, preferably but not necessarily a superdisintegrant, such that the initial step of the process provides active agent granules, while the remainder of the formulation that is later blended in contains a lubricant, additional disintegrant, and additional porous binder. When an absorption enhancing composition is used, it is normally incorporated in the initial step along with the active agent. In a variation of this method, a dry granulation technique may be employed in which the steps are somewhat analogous but the first step of the process involves roller compaction or slugging of the combined components followed by granulation, and the mixture does not contain a liquid.

In a further embodiment, the invention provides a way to evaluate and select component(s) that may advantageously serve as the absorption enhancing composition herein, i.e., the composition that improves the absorption of the active agent by reducing precipitation and/or aggregation of the agent as the agent transitions from the stomach to the higher pH environment of the duodenum. The method involves measurements of light transmitted at regular time intervals after the pH of an aqueous solution containing the active agent and the candidate absorption enhancing composition is increased from 2.5 to 7.0, and comparing the results obtained with that of a control experiment in which no candidate absorption enhancing composition is present. Increase in transmission, as a general rule, is indicative of a reduction in precipitation and/or aggregation induced by the presence of the candidate absorption enhancing composition. Accordingly, the method comprises: (a) dissolving the active agent in an acidic solution, gradually increasing the pH of the solution until a pH of about 7.0 is reached, and then monitoring the extent of precipitation of the active agent over time as the solution becomes a suspension, by measuring the fraction of light transmitted through the suspension at regular time intervals following the increase in pH; (b) dissolving the active agent and a candidate composition in an acidic solution, gradually increasing the pH of the solution until a pH of about 7.0 is reached, and then monitoring the extent of precipitation of the active agent over time as the solution becomes a suspension, by measuring the fraction of light transmitted through the suspension at regular time intervals following the increase in pH; and (c) evaluating the capability of a candidate composition to enhance the absorption of a basic active agent in the duodenum by comparing the fraction of light transmitted in (b) to the fraction of light transmitted in (a) at each time interval.

Those candidate compositions that are found to increase the fraction of light transmitted at one or more time intervals are selected as absorption enhancers, with preferred absorption enhancers capable of increasing the fraction of light transmitted over a prolonged time period, e.g., at least 5-15 minutes. It will be appreciated that the method is useful in conjunction with screening candidate compositions that will enhance the duodenal absorption of basic active agents in general, and is not limited to avanafil per se.

The disclosure provides an orally disintegrating tablet, comprising the following: a therapeutically effective amount of avanafil; an absorption enhancing composition comprising a surfactant; an orally disintegrating composition comprising a disintegrant; and a porous component in a pharmaceutically acceptable carrier. In certain embodiments of the tablets of the disclosure, the tablet does not comprise fumaric acid, tartaric acid, succinic acid, malic acid, ascorbic acid or aspartic acid.

Tablets of the disclosure may be designed to disintegrate within an oral cavity within in less than a minute while exhibiting a minimal hardness. In certain embodiments of the tablets of the disclosure, the tablet disintegrates within an oral cavity within about 45 seconds and exhibits a hardness of greater than about 30 N. In certain embodiments of the tablets of the disclosure, the tablet disintegrates within an oral cavity within about 30 seconds and exhibits a hardness of greater than about 15 N. In certain embodiments of the tablets of the disclosure, the tablet disintegrates within an oral cavity within about 15 seconds and exhibits a hardness of greater than about 7.5 N. Disintegrants of the tablets of the disclosure may be superdisintegrants.

Porous components of the tablets of the disclosure may, for example, comprise porous mannitol.

Surfactants of the tablets of the disclosure may comprise a polymeric component that mitigates the precipitation of avanafil in an aqueous medium as pH increases from about 2.5 to about 7.0. In certain embodiments, the polymeric component of a tablet of the disclosure is nonionic and mitigates the precipitation of avanafil in an aqueous medium as pH increases from about 2.5 to about 7.0 by delaying precipitation, reducing the rate of precipitation, decreasing the extent of precipitation, or any combination of the foregoing. Polymeric components of the tablets of the disclosure may comprise a hydrophilic segment and a hydrophobic segment. Polymeric components of the tablets of the disclosure may comprise a polyoxyethylene-polyoxypropylene copolymer. Polymeric components of the tablets of the disclosure may comprise poloxamer 407.

The proportion of avanafil in a tablet of the disclosure may comprise or consist of about 10 wt. % to about 50 wt. % of the tablet. The proportion of avanafil in a tablet of the disclosure may comprise or consist of 10 wt. % to 50 wt. % of the tablet. In other words, in a tablet of the disclosure, the avanafil or proportion of avanafil may represent in the range of about 10 wt. % to about 50 wt. % of the tablet.

The proportion of avanafil in a tablet of the disclosure may comprise or consist of about 70 wt. % of the tablet. The proportion of avanafil in a tablet of the disclosure may comprise or consist of 70 wt. % of the tablet. In other words, in a tablet of the disclosure, the avanafil or proportion of avanafil may represent up to about 70 wt. % of the dosage form.

The disclosure provides a method for administering a PDE V inhibitor to a subject having a PDE V inhibitor-treatable condition selected from erectile dysfunction, hypertension, angina pectoris, myocardial infarction, heart failure, pulmonary arterial hypertension, prostatic hyperplasia, female sexual dysfunction, neurogenesis, neuropathy, Alzheimer's disease, psoriasis, skin necrosis, metastasis, baldness, nutcracker oesophagus, anal fissure, hemorrhoids, insulin resistance syndrome, hypoxic vasoconstriction, and blood pressure stabilization, comprising orally administering the tablet according to claim 1 to the subject on an as-needed basis.

The disclosure provides method for manufacturing a rapidly disintegrating oral dosage form, comprising: (a) preparing active agent granules by (i) blending a pharmacologically active agent in particulate form with a first fraction of a disintegrant and a first fraction of a porous binder, to form an initial mixture, and (ii) granulating the initial mixture for a predetermined time period at a predetermined temperature, to provide the active agent granules; (b) blending the active agent granules with a lubricant, a second fraction of a disintegrant, and a second fraction of a porous binder, to provide a final formulation mixture; and (c) compacting the final formulation mixture to prepare the rapidly disintegrating oral dosage form. In certain embodiments of the methods of manufacturing a tablet of the disclosure, the granulating step is carried out in a solvent and step (a) further comprises drying the granulation prepared in (ii) prior to step (b).

In certain embodiments of the methods of manufacturing a tablet of the disclosure, the porous binder is selected from porous mannitol, porous lactose, and porous glucose and wherein the disintegrant comprises at least one superdisintegrant.

In certain embodiments of the methods of manufacturing a tablet of the disclosure, the active agent is avanafil and the method further comprises incorporating an absorption enhancing composition into the dosage form, wherein a first fraction of the absorption enhancing composition is incorporated in (a) and a second fraction of the absorption enhancing composition is incorporated in (b).

The disclosure provides a tablet made or manufactured by any method of the disclosure. For example, the disclosure provides an orally disintegrating tablet having hardness of 13.5 N or more, which is obtained by a process comprising the following steps: (a) preparing active agent granules by (i) blending avanafil in particulate form with a first fraction of a disintegrant and a first fraction of a porous binder, to form an initial mixture, and (ii) granulating the initial mixture for a predetermined time period at a predetermined temperature, to provide the active agent granules, wherein granulating is carried out in a solvent; (b) drying the active agent granules; (c) blending the dry active agent granules with a lubricant, a second fraction of the disintegrant, and a second fraction of a porous binder, to provide a final formulation mixture; and (d) compacting the final formulation mixture to prepare the rapidly disintegrating oral dosage form.

Other aspects, embodiments, advantages, and variations of the invention will be apparent to those of ordinary skill in the art based on the description herein and the knowledge of those working in the pertinent fields.

DETAILED DESCRIPTION OF THE INVENTION

Figure 1:
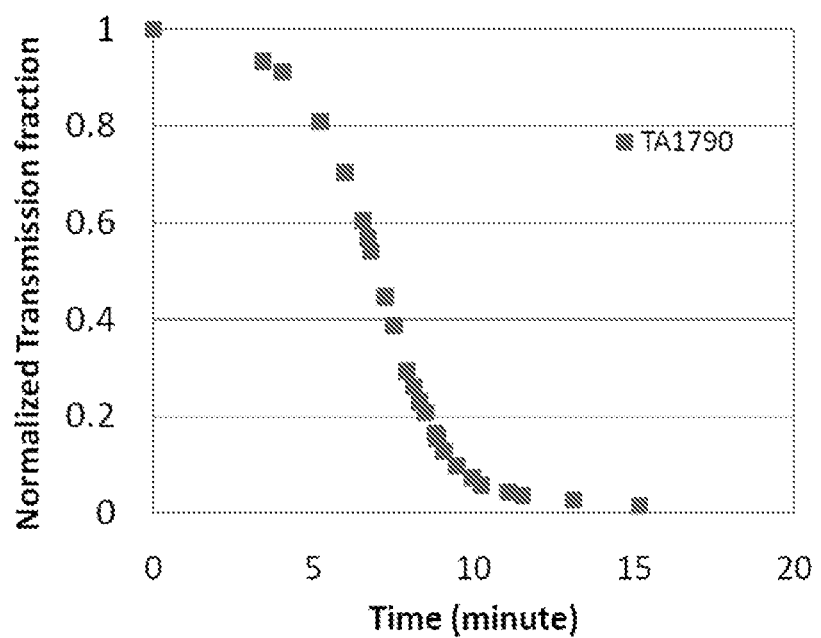
FIG. 1 is a graph of normalized transmission fraction versus time for the control experiment described in Example 2.

Unless otherwise indicated, the invention is not limited to specific formulation components, dosage regimens, manufacturing processes, absorption enhancer evaluation techniques, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an active agent" or "a pharmacologically active agent" includes a single active agent as well as a combination or mixture of two or more different active agents, reference to "an absorption enhancing composition" includes reference to a single such composition or a mixture of such compositions (with each such composition itself including one or more individual components), reference to "a carrier" or "an excipients" includes mixtures of two or more carriers and two or more excipients as well as a single carrier or excipient, and the like.

In describing and claiming the present invention, the following terminology will be used in accordance with the definitions set out below.

The terms "active agent," "pharmacologically active agent" and "drug" are used interchangeably herein to refer to a chemical compound that induces a desired pharmacological, physiological effect, i.e., in this case, treatment of erectile dysfunction. The primary active agents herein are inhibitors of phosphodiesterase V ("PDE V inhibitors"). The aforementioned terms also encompass pharmaceutically acceptable, pharmacologically active derivatives of those active agents specifically mentioned herein, including, but not limited to, salts, esters, amides, prodrugs, active metabolites, conjugates, analogs, and the like. When the terms "active agent," "pharmacologically active agent" and "drug" are used, then, or when a particular active agent is specifically identified, it is to be understood that the term includes not only the active agent per se but also its pharmaceutically acceptable, pharmacologically active salts, esters, amides, prodrugs, metabolites, conjugates, analogs, etc.

By pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective in the treatment of premature ejaculation. "Carriers" or "vehicles" as used herein refer to conventional pharmaceutically acceptable carrier materials suitable for drug administration, and include any such materials known in the art that are nontoxic and do not interact with other components of a pharmaceutical composition or drug delivery system in a deleterious manner.

The term "erectile dysfunction" is intended to include any and all types of erectile dysfunction, including: vasculogenic, neurogenic, endocrinologic and psychogenic impotence ("impotence" is used here in its broadest sense to indicate a periodic or consistent inability to achieve or sustain an erection of sufficient rigidity for sexual intercourse (see U.S. Pat. No. 5,242,391 to Place et al.); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, Disorders of Sexual Desire (New York, N.Y. Brunner Mazel Book Inc., 1979)).

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" erectile dysfunction, as the term is used herein, thus encompasses both prevention of the disorder in a predisposed individual and treatment of the disorder in a clinically symptomatic individual.

By an "effective" amount or a "therapeutically effective amount" of a drug or pharmacologically active agent is meant a nontoxic but sufficient amount of the drug or agent to provide the desired effect. The amount that is "effective," however, will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

By "as-needed" dosing, also referred to as "pro re nata" dosing, "pm" dosing, and "on-demand" dosing or administration, is meant the administration of an active agent at a time just prior to the time at which drug efficacy is wanted, e.g., just prior to anticipated sexual activity, and within a time interval sufficient to provide for the desired therapeutic effect, i.e., enhancement in sexual desire and in sexual responsiveness during sexual activity. "As-needed" administration herein does not involve priming doses or chronic administration, "chronic" meaning administration at regular time intervals on an ongoing basis. As-needed administration may involve administration immediately prior to sexual activity, but will generally be about 0.25 to 3.5 hours, preferably about 0.5 to 3 hours, and most preferably about 1 to 2.5 hours prior to anticipated sexual activity. "As-needed" administration may or may not involve administration of a sustained release formulation in advance of anticipated sexual activity, with drug release taking place throughout an extended drug delivery period typically in the range of about 4 to 72 hours.

The term "orally disintegrating tablet" (ODT) is used interchangeably with the term "rapidly disintegrating tablet" (RDT) to refer to a solid dosage form composed of a tablet that is designed to disintegrate or dissolve rapidly in the oral cavity without need for chewing or swallowing with liquids. Preferred orally disintegrating tablets herein have the characteristics set forth by the U.S. Food & Drug Administration in *Guidance for Industry: Orally Disintegrating Tablets* (Dept. of Health and Human Services, U.S. FDA Center for Drug Evaluation and Research, December 2008). Generally, then, the preferred tablets of the invention exhibit in vitro disintegration times of 30 seconds or less when evaluated using the USP Disintegration Test described in USP 24-NF 19 or an equivalent alternative test. As explained in the foregoing section of the U.S Pharmacopoeia, the USP Disintegration Test is conducted by placing the dosage form to be tested in a basket rack assembly, immersing the assembly in a specified fluid at a temperature between 35° C. and 39° C. for a given time period, and raising and lowering the basket in the immersion fluid through a distance of about 5.5 cm at a frequency of about 30 cycles per minute. The dosage forms are visually inspected at specified times for complete disintegration, defined in Section 701 of USP 24-NF 19 as the state in which any residue of the dosage form remaining in the basket rack of the test apparatus is a "soft mass having no palpably firm core." As such, it will be appreciated that the present dosage forms are optimal for rapid disintegration in the mouth without the need to drink additional water. Adsorption may be through the duodenum or through the oral mucosa.

Active Agents:

In one embodiment, then, an oral dosage form is provided for the administration and rapid absorption of avanafil. Unless otherwise indicated, reference to avanafil encompasses avanafil per se as well as N-heterocycle-substituted ketones having the structure of Formula (I)

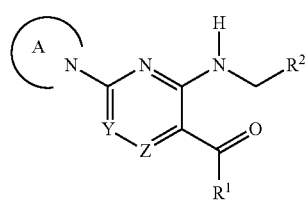

(I)

wherein: Ring A is a substituted or unsubstituted nitrogen-containing heterocyclic group; $R^1$ is a substituted or unsubstituted lower alkyl group, a substituent having the formula —NH-Q-$R^3$ wherein Q is a lower alkylene group or a single bond and $R^3$ is a substituted or unsubstituted nitrogen-containing heterocyclic group, or a substituent having the formula —NH—$R^4$ wherein $R^4$ is substituted or unsubstituted cycloalkyl; $R^2$ is substituted or unsubstituted aryl; and one of Y and Z is =CH— and the other is =N—, and also include pharmaceutically acceptable salts of the compounds.

Among the aforementioned compounds, the nitrogen-containing heterocyclic group of the "substituted or unsubstituted nitrogen-containing heterocyclic group" for Ring A is a 5- to 10-membered monocyclic or bicyclic nitrogen-containing heterocyclic group, more particularly, a 5- or 6-membered nitrogen-containing heteromonocyclic group and an 8- to 10-membered nitrogen-containing heterobicyclic group, and most particularly, a 5- or 6-membered non-aromatic nitrogen-containing heteromonocyclic group such as pyrrolidinyl, piperazinyl, piperidyl, morpholino, etc., a 5- or 6-membered aromatic nitrogen-containing heteromonocyclic group such as imidazolyl or pyrrolyl, etc., and a nitrogen-containing heterobicyclic group such as 6,7-dihydro-5H-pyrrolo[3,4-b]pyridin-6-yl, 5,6,7,8-tetrahydroimidazo[1,2-a]-pyrazin-7-yl, 5,6,7,8-tetrahydro-1,7-naphthyridin-7-yl, 1,2,3,4-tetrahydro-2-isoquinolinyl, 1H-2,3,4,5,6,7-hexahydropyrazolo[4,3-c]pyridin-5-yl, 4,5,6,7-tetrahydrothiazolo[5,4-c]-pyridin-6-yl, 5,6,7,8-tetrahydropyrido[4,3-d]pyrimidin- 6-yl, 4,5,6,7-tetrahydro-3H-imidazo[4,5-c]pyridin-3-yl, etc.

The nitrogen-containing heterocyclic group of the "substituted or unsubstituted nitrogen-containing heterocyclic group" for $R^3$ is a 5- or 6-membered nitrogen-containing heteromonocyclic group or an 8- to 10-membered nitrogen-containing heterobicyclic group, for example, a 5- or 6-membered non-aromatic nitrogen-containing heteromonocyclic group such as morpholinyl, piperazinyl, piperidyl, thiadiazolyl, dihydropyrimidinyl, dihydropyrazolyl, a 5- or 6-membered aromatic nitrogen-containing heteromonocyclic group such as pyrimidinyl, pyridazinyl, pyridyl, pyrazolyl, imidazolyl, oxazolyl, thiazolyl, pyrazinyl, and an 8- to 10-membered nitrogen-containing heterobicyclic group such as benzothiazolyl quinolyl, dihydrobenzoxazolyl, etc.

The substituent of the "substituted or unsubstituted nitrogen-containing heterocyclic group" for Ring A and $R^3$, i.e., when the nitrogen-containing heterocyclic group is substituted, is, for example, (1) a lower alkyl group, (2) a hydroxy-substituted lower alkyl group, (3) a formyl group, (4) an oxo group, (5) an amino group, (6) a di-(lower alkyl)amino group, (7) a hydroxy group, (8) a lower alkoxy group, (9) a lower alkoxycarbonyl group, (10) a lower alkoxy-substituted lower alkanoyl group, (11) a lower alkanoyl group, (12) a cyano-substituted lower alkyl group, or (13) a pyrimidinyl group substituted by (i) a benzylamino group substituted by a halogen atom and a lower alkoxy group and (ii) a cycloalkylcarbamoyl group substituted by a hydroxy group, etc.

The aryl group of the "substituted or unsubstituted aryl group" for $R^2$ is, for example, a 5- to 10-membered monocyclic or bicyclic aromatic hydrocarbon group such as phenyl group, naphthyl group, etc.

The substituent of the "substituted or unsubstituted aryl group" for $R^2$, when $R^2$ is a substituted aryl group, is, for example, a lower alkoxy group, a halogen atom, a cyano group, a nitro group, a hydroxy group, a lower alkyl group, etc.

The substituent of the "substituted or unsubstituted lower alkyl group" for $R^1$ and the substituent of the "substituted or unsubstituted cycloalkyl group" for $R^4$, i.e., when $R^1$ and $R^4$ are substituted lower alkyl and substituted cycloalkyl, respectively, are, for example, a lower alkoxy group, a hydroxy group, a morpholinyl group, a lower alkylsulfonyl group, a di-(lower alkyl)phosphino group, a di-(lower alkyl) amino group, a pyrimidinyl-substituted lower alkylamino group, a pyridyl group, a pyridylamino group, a lower alkyl-substituted piperazinyl group, a pyrimidinyloxy group, etc.

It should be noted with respect to the above that a "lower alkyl group" refers to a straight chain or branched chain alkyl group having 1 to 6 carbon atoms, such as methyl, ethyl, propyl, isopropyl, butyl, isobutyl, tert-butyl, etc., while a "lower alkoxy group" refers to a straight chain or branched chain alkoxy group having 1 to 6 carbon atoms, such as methoxy, ethoxy, propoxy, isopropyloxy, butyloxy, isobutyloxy, tert-butyloxy, etc.

A "cycloalkyl group" refers to a cycloalkyl group having 3 to 8 carbon atoms, such as cyclopropyl, cyclobutyl, cyclopentyl, cyclohexyl, cycloheptyl, etc. A "lower alkylene group" refers to a straight chain or branched chain alkylene group having 1 to 6 carbon atoms, such as methylene, ethylene, trimethylene, etc.

A "halogen" substituent or a "halogen atom" refers to a fluoro, chloro, bromo, or iodo substituent.

Among the compounds (I) of the present invention, preferred compounds are those wherein the nitrogen-containing heterocyclic group of the "substituted or unsubstituted nitrogen-containing heterocyclic group" for Ring A is a 5- or 6-membered nitrogen-containing heteromonocyclic group or an 8- to 10-membered nitrogen-containing heterobicyclic group, and the substituent of the above "substituted or unsubstituted nitrogen-containing heterocyclic group" is selected from (1) a lower alkyl group, (2) a hydroxy-substituted lower alkyl group, (3) a formyl group, (4) an oxo group, (5) an amino group, (6) a hydroxy group, (7) a lower alkoxycarbonyl group, and (8) a pyrimidinyl group substituted by (i) a benzylamino group substituted by a halogen atom and a lower alkoxy group and (ii) a cycloalkylcarbamoyl group substituted by a hydroxy group, $R^1$ is a lower alkyl group which may optionally be substituted by a group selected from a lower alkoxy group, a hydroxy group, a morpholinyl group, a lower alkylsulfonyl group, a di-(lower alkyl)phosphino group, a di-(lower alkyl)amino group, a pyrimidinyl-substituted lower alkylamino group, a pyridyl group, a pyridylamino group, and a lower alkyl-substituted piperazinyl group, a group of the formula —NH-Q-$R^3$, or a group of the formula —NH—$R^4$, the nitrogen-containing heterocyclic group of the "substituted or unsubstituted nitrogen-containing heterocyclic group" for $R^3$ is a 5- or 6-membered nitrogen-containing heteromonocyclic group or an 8- to 10-membered nitrogen-containing heterobicyclic group, and the substituent of the above "substituted or unsubstituted nitrogen-containing heterocyclic group" is selected from a lower alkyl group, a hydroxy-substituted lower alkyl group, an oxo group, an amino group, a di-(lower alkyl)amino group, a lower alkanoyl group and a cyano-substituted lower alkyl group, $R^4$ is a cycloalkyl group substituted with a group selected from hydroxy, a lower alkoxy, and pyrimidinyloxy, $R^2$ is a phenyl group substituted with a group selected from lower alkoxy, a halogen atom, cyano, nitro, hydroxy, and lower alkyl.

Preferred subsets of these compounds are described in U.S. Pat. No. 6,656,935 to Yamada et al., the disclosure of which is incorporated by reference in its entirety herein. Avanafil per se, compound (II), is particularly preferred.

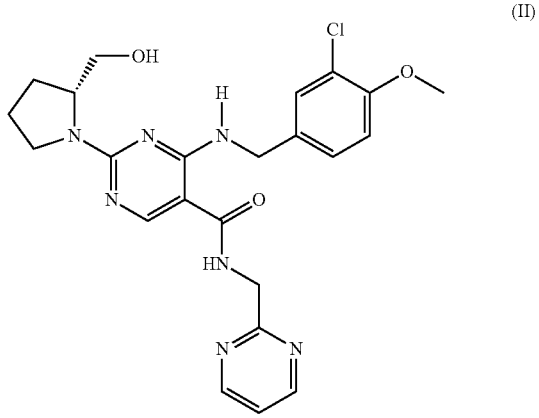 [SMILES: COc1ccc(CNc2nc(N3CCC[C@@H]3CO)ncc2C(=O)NCc2ncccn2)cc1Cl]

(II)

The avanafil is incorporated into the dosage form as a particulate composition, with smaller particles preferred to provide increased surface area and thus assist in enabling maintenance of a high absorption rate (as the absorption of avanafil involves primarily a passive diffusion process). Generally, the avanafil particles will have an average diameter in the range of about 5 nm to about 5000 µm, and a preferred range is about 5 µm to about 1000 µm. Particulate avanafil can be obtained from Tanabe Seiyaku Co., Ltd. (Osaka, JP).

The active agent may be incorporated into the formulations of the invention as a salt, prodrug, metabolite, analog, isomer, etc., provided that the salt, prodrug, metabolite, analog, isomer, etc. is pharmaceutically acceptable and, with the exception of prodrugs, pharmacologically active as well. These derivatives may be prepared using standard procedures known to those of ordinary skill in the art and described, for example, by J. March, *Advanced Organic Chemistry: Reaction, Mechanisms, and Structure*, $4^{th}$ edition (New York: Wiley-Interscience, 1992).

For instance, acid addition salts of the active agent can be prepared using conventional methodology involving the reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. See, for example, U.S. Pat. No. 7,501,409. An acid addition salt may be reconverted to the free base by treatment with a suitable base. In most embodiments herein, however, it is preferred that the active agent be incorporated into the formulations and dosage forms of the invention as the free base.

Formulations:

The avanafil formulations are adapted for oral drug administration, and are orally disintegrating tablets (also sometimes referred to as "rapidly disintegrating tablets," as described earlier herein). In order to improve the absorption of the active agent, the formulations of the invention contain a absorption enhancing composition, i.e., a composition selected to reduce precipitation and aggregation of avanafil particles as the particulate avanafil, dissolved in the stomach, passes into the far more basic environment of the duodenum. The absorption enhancing composition thus facilitates greater absorption of the avanafil in the body, in turn making the drug far more effective at a given dosage. The composition, as noted, preferably is or contains a polymeric component, and preferably is or contains an amphiphilic component, i.e., a component that has at least one hydrophilic segment and at least one hydrophobic segment, as will be detailed infra. In a preferred embodiment, the absorption enhancing composition comprises an amphiphilic polymer such as a nonionic surfactant.

Suitable absorption enhancing compositions are best selected using a simple and straightforward process as will be described infra. Any compositions that are pharmaceutically acceptable and which do not adversely interact with the active agent or any other components of the formulation may be used, so long as they are determined to be effective according to the process described herein. The term "polymeric" is meant to describe preferred component(s) of the absorption enhancing composition refers to a molecule containing two or more covalently attached monomer units, and includes branched, dendrimeric, and star polymers as well as linear polymers. The term also includes both homopolymers and copolymers, e.g., random copolymers, block copolymers, graft copolymers, and uncrosslinked polymers, as well as slightly, moderately, and substantially crosslinked polymers. Many such suitable compositions also contain one or more components composed of at least one hydrophilic segment and at least one lipophilic (hydrophobic) segment, where those terms are used according to their usual definitions. See also Aungst, B. J. (2012) AAPS 14(1):P10-18.

Avanafil's solubility profile as a function of pH makes it a transient class II drug having good solubility in a low pH environment, such as the stomach, but potentially slow absorption kinetics if the low solubility in high pH (greater than 5.0) is the limiting step. An ODT tablet melts quickly in the mouth and is likely fully dissolved in the stomach before the avanafil enters the duodenum where the pH is about 6.8. A key parameter is how quickly the dissolved avanafil precipitates upon entering the duodenum. Slowing the precipitation long enough to allow absorption can be used to achieve the desired pharmacokinetic outcome. Surfactant based formulations may be used to prevent aggregation of avanafil particles to reduce precipitation and speed absorption relative to precipitation since lower surface area leads to faster absorption kinetics.

Examples of preferred polymeric components that may be incorporated into or serve as the absorption enhancing composition are thus surfactants. That is, to function as a surfactant, a compound must necessarily be amphiphilic, i.e. include polar or charged hydrophilic moieties, as well as non-polar lipophilic (hydrophobic) moieties. An empirical parameter commonly used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value; see, e.g., Schott (1990) *J. Pharm. Sci.* 12(1):87-88. Likewise, for certain polypropylene oxide-containing block copolymers (e.g., the Pluronic® surfactants, available from BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the formulations of the present invention. Preferred surfactants herein that are incorporated into or serve as the absorption enhancing composition generally have an HLB of at least 10, with more preferred surfactants having an HLB of at least 12; the preferred surfactants herein, and the preferred absorption enhancing compositions herein, are thus hydrophilic.

Suitable surfactants for use as or in the absorption enhancing composition can be anionic, cationic, zwitterionic or non-ionic, although non-ionic surfactants are preferred, particularly non-ionic hydrophilic surfactants. Mixtures of surfactants as well as mixtures of surfactants with non-surfactant or non-polymeric absorption enhancing components and compositions are also within the scope of the invention.

Surfactants useful herein include, but are not limited to, nonionic surfactants such as polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, and lower alcohol fatty acid esters; and ionic surfactants as will be detailed below. Nonionic surfactants are preferred as or in the absorption enhancing composition, and may be either un-ionizable surfactants or ionizable surfactants that are in un-ionized form. Preferred nonionic surfactants, i.e., un-ionizable surfactants, are as follows:

Polyethylene Glycol Fatty Acid Esters: Although polyethylene glycol itself does not function as a surfactant, a variety of PEG-fatty acid esters, such as PEG-fatty acid monoester, PEG-fatty acid diesters, and PEG-fatty acid mono- and di-ester mixtures have useful surfactant properties. Among the PEG-fatty acid esters, esters of caproic acid, caprylic acid, capric acid, lauric acid, oleic acid, stearic acid, linoleic acid, and linolenic acid are especially useful.

Alcohol-Oil Transesterification Products: A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, maltol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred lipophilic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol M40), and PEG-20 almond glycerides (Crovol A40).

Polyglycerized Fatty Acids: Among the polyglyceryl fatty acid esters, preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Preferred lipophilic surfactants include polyglyceryl oleate (Plurol Oleique), polyglyceryl-2 dioleate (Nikkol DGDO), and polyglyceryl-10 trioleate.

Propylene Glycol Fatty Acid Esters: Both mono- and diesters of propylene glycol may be used. In this surfactant class, preferred lipophilic surfactants include Capryol 90, Labrafac PG, propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Mono- and Diglycerides: Other suitable surfactants are the mono- and diglycerides. These surfactants are generally lipophilic. Preferred lipophilic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul® MCM), caprylic acid mono/diglycerides (Inmwitor®988), and mono- and diacetylated monoglycerides (Myvacet® 9-45).

Sterol and Sterol Derivatives: Sterols and derivatives of sterols are can be hydrophilic or hydrophobic. Preferred derivatives include polyethylene glycol derivatives, and preferred hydrophilic surfactants in this class are PEG-24 cholesterol ether (Solulan® C-24), PEG-30 cholestanol (Nikkol® DHC), and phytosterol (GENEROL® series, Henkel).

Sorbitan Fatty Acid Esters and Polyethylene Glycol Sorbitan Fatty Acid Esters: A variety of sorbitan esters of fatty acids may be used as or in the present absorption enhancing composition. Among these esters, preferred hydrophilic surfactants include PEG-sorbitan fatty acid esters, such as PEG-20 sorbitan monolaurate (Tween 20), PEG-20 sorbitan monopalmitate (Tween 40), PEG-20 sorbitan monostearate (Tween 60), and PEG-20 sorbitan monooleate (Tween 80).

Sugar Esters: Preferred surfactants in this class include sucrose monolaurate, sucrose monopalmitate, sucrose distearate/monostearate, and sucrose acetate isobutyrate. Examples of commercially available such surfactants are the sucrose stearates available as Surfhope® SE D-1803F, D-1805, D-1807, D-1809, D-1811, D-1811F, D-1815, and D-1816 (HLB 3, 5, 7, 9, 11, 11, 15, and 16, respectively) from Mitsubishi-Kagaku, sucrose palmitate available as Surfhope® SE D-1615 and D-1616 (HLB 15 and 16, respectively), and sucrose laurate available as Surfhope® SE D-1216 (HLB 16), also from Mitsubishi-Kagaku.

Polyethylene Glycol Alkyl Ethers and Polyethylene Glycol Alkyl Phenol Ethers: Ethers of polyethylene glycol and alkyl alcohols or phenols are also suitable surfactants for use in the present invention. Preferred ethers include PEG-3 oleyl ether (Volpo 3), PEG-4 lauryl ether (Brij 30), and PEG-10-100 nonyl phenol (Triton X series Rohm & Haas).

Polyoxyethylene-Polyoxypropylene ("POE-POP") Block Copolymers: The POE-POP block copolymers are a unique class of polymeric surfactants. The unique structure of the surfactants, with hydrophilic POE and hydrophobic POP moieties in well-defined ratios and positions, provides a wide variety of surfactants that are suitable herein. These surfactants are available under various trade names, including Synperonic® PE series (ICI); Pluronic® (series (BASF), Emkalyx®, Lutrol® (BASF), Supronic®, Monolan®, Pluracare®, and Plurodac®. The generic term for these polymers is "poloxamer" (CAS 9003-11-6). These polymers have the formula

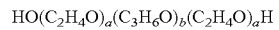

wherein "a" and "b" denote the number of polyoxyethylene and polyoxypropylene units, respectively. All of the poloxamers are chemically similar in terms of their composition, differing only in the relative amounts of propylene oxide and ethylene oxide monomer units added during manufacture and thus incorporated into the final block copolymer. Preferred hydrophilic surfactants of this class include Poloxamers 108, 188, 217, 238, 288, 338, and 407. Preferred hydrophobic surfactants in this class include Poloxamers 124, 182, 183, 212, 331, and 335. Poloxamer 407 is particularly preferred as or in the absorption enhancing compositions herein. Other block copolymers, particularly of the A-B-A type where the A blocks are relatively hydrophobic and the B block is relatively hydrophilic can also be used.

Lower Alcohol Fatty Acid Esters: Esters of lower alcohols ($C_2$ to $C_4$) and fatty acids ($C_8$ to $C_{18}$) are suitable surfactants for use in the present formulations. Among these esters, preferred hydrophobic surfactants include ethyl oleate (Crodamol EO), isopropyl myristate (Crodamol IPM), and isopropyl palmitate (Crodamol IPP).

Ionizable Surfactants: Ionizable surfactants, when present in neutral, uncharged form, are also nonionic surfactants Particular examples of such surfactants include free fatty acids, particularly $C_6$-$C_{22}$ fatty acids, and bile acids. More specifically, suitable unionized ionizable surfactants include the free fatty acid and bile acid forms of any of the fatty acid salts and bile salts. Preferred ionizable surfactants include fatty acids and their corresponding salts, such as caprylic acid/sodium caprylate, oleic acid/sodium oleate, capric acid/sodium caprate; ricinoleic acid/sodium ricinoleate, linoleic acid/sodium linoleate, and lauric acid/sodium laurate; trihydroxy bile acids and their salts, such as cholic acid (natural), glycocholic acid and taurocholic acid; dihydroxy bile acids and their salts, such as deoxycholic acid (natural), glycodeoxycholic acid, taurodeoxycholic acid, chenodeoxycholic acid (natural), glycochenodeoxycholic acid, taurochenodeoxycholic acid, ursodeoxycholic acid, tauroursodeoxycholic acid, and glycoursodeoxycholic acid; monohydroxy bile acids and their salts, such as lithocholic acid (natural); sulfated bile salt derivatives; sarchocholate; fusidic acid and its derivatives; phospholipids, such as phosphatidyl choline, phosphatidyl ethanolamine, phosphatidyl serine, PD inositol, lysolecithin, and palmitoyl lysophosphatidyl choline; carnitines, such as palmitoyl camitine, lauroyl camitine and myristoyl carnitine; cyclodextrins, including alpha, beta and gamma cyclodextrins; and modified cyclodextrins, such as hydroxypropyl and sulfobutyl ether.

Ionic Surfactants: Ionic surfactants, including cationic, anionic and zwitterionic surfactants, may also be used. Preferred ionic surfactants include fatty acid salts, bile salts, phospholipids, carnitines, ether carboxylates, succinylated monoglycerides, mono/diacetylated tartaric acid esters of mono- and diglycerides, citric acid esters of mono-, diglycerides, alginate salts, and lactylic esters of fatty acids. Specifically, preferred ionic surfactants include sodium oleate, sodium lauryl sulfate, sodium lauryl sarcosinate, sodium dioctyl sulfosuccinate, sodium cholate, sodium taurocholate, lauroyl carnitine; palmitoyl carnitine; and myristoyl carnitine. It will be appreciated by one skilled in the art, however, that any bioacceptable counterion may be used. For example, although the fatty acids are shown as sodium salts, other cation counterions can also be used, such as alkali metal cations or ammonium. In contrast to typical non-ionic surfactants, these ionic surfactants are generally available as pure compounds.

It should be noted that the rapidly disintegrating tablets of the invention may be placed on the tongue, or they may be sublingual or buccal dosage forms. Such dosage forms have significant advantages, particularly for patients who are unable or unwilling to swallow a tablet or capsule. The rapidly disintegrating dosage forms herein also enable on-demand drug administration that provides for effective blood levels of the active agent in a relatively short period of time, an advantage that is useful with, for instance, erectile dysfunction drugs such as avanafil to be taken prior to sexual activity.

In addition to the active agent and the absorption enhancing composition, the formulation contains a "pharmaceutically acceptable carrier," which in the present context generally comprises a plurality of components, including, typically, at least one binder, at least one of which is preferably porous, at least one disintegrant, and other components selected from diluents, lubricants, glidants, colorants, flavoring agents, sweeteners, preservatives, and the like.

Binders, also sometimes referred to in the art as granulators, are selected to provide cohesiveness to a dosage form, ensuring that the dosage form, e.g., a tablet, remains intact after preparation via compaction or the like. Typical binders useful herein include, without limitation, starch; gelatin; waxes; pectins; sugars such as sucrose, glucose, dextrose, molasses, and lactose; gums such as acacia, guar gum, and sodium alginate; polyethylene glycol; hydrophilic polymers such as acrylic acid polymers and copolymers thereof, e.g., those known as carbomers (Carbopol®, B.F. Goodrich, is one such polymer), polyvinyl alcohol, polyvinylpyrrolidone; and cellulosic polymers such as hydroxypropyl methylcellulose (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

As alluded to above, the present formulations preferably include, as a single binder component or as one of two or more binder components, a porous component that serves to increase bulk density of the formulation, which in turn enables preparation of tablets of greater hardness than otherwise possible. Hardness, as is understood in the art, is a measure of the cohesiveness of a tablet or other dosage form, and is sometimes equated with tensile strength. Preferred porous binders herein are directly compressible, water soluble carbohydrates such as mannitol, lactose, sucrose, xylose, trehalose, dextrose, and the like, with directly compressible porous mannitol, porous lactose, and porous glucose particularly preferred. Such components can also serve as disintegrants and superdisintegrants; see infra.

Disintegrants: Disintegrants are used to facilitate dosage form disintegration after administration. Typical disintegrants that may be used in conjunction with the present invention include, by way of example: starch, starch derivatives such as sodium carboxymethyl starch, pregelatinized starch, and sodium starch glycolate; cellulose and cellulosic materials such as sodium carboxymethylcellulose, other salts of carboxymethylcellulose, hydroxypropyl cellulose, and crosslinked cellulosic materials such as crosslinked carboxymethylcelluloses, e.g., croscarmelose (e.g., Ac-di-Sol®, FMC; U.S. Pat. No. 5,456,921); clays such as bentonite; gum and gum-like materials such as alginic acid, sodium alginate, guar gum, Veegum® HV; and other cross-linked materials such as cross-linked polyvinylpyrrolidone or "crospovidone" (e.g., Polyplasdone® XL, GAF).

Preferred disintegrants herein are those commonly referred to as "superdisintegrants," which facilitate rapid disintegration of the present oral dosage forms following introduction into the oral cavity. Superdisintegrants are referred to as such because of their high efficiency, even at low levels (e.g., 2 wt. % to 4 wt. %; see Remington's, supra). Superdisintegrants are also swellable in water, and thus include numerous swellable crosslinked materials, including crosslinked celluloses such as croscarmelose, crosslinked hydrophilic polymers such as crospovidone, and crosslinked starches such as sodium starch glycolate (e.g., available as Explotab® and Explotab CLV®, Penwest Pharmaceuticals Co.). Some materials, as is known in the art, serve multiple functions in oral dosage forms; for instance, microcrystalline cellulose (e.g., Avicel PH1010 and Avicel PH1020, from FMC; Emocel®, from Edward Mendell Co., Inc.), described in U.S. Pat. Nos. 2,978,446, 3,141,875, and 3,023,104, is useful both as a binding agent and as a superdisintegrant. Starch-based superdisintegrants used herein may also be combined with an augmenting agent as described in U.S. Pat. No. 6,660,303 to Staniforth), to increase compactibility of the formulation without compromising disintegration kinetics. See also, Mohanachandra et al. 2011 *Int. J. of Pharma. Sciences Rev. and Res.* 6(1):105-109.

Particularly preferred superdisintegrants herein, which can also serve as binders, obviating the need for additional binder components if desired, are directly compressible spray dried carbohydrates, such as directly compressible mannitol, sorbitol, maltitol, lactose, etc. Directly compressible spray dried mannitol, comprising particles having a diameter of from about 20 μm to about 200 μm, e.g., from about 50 μm to about 175 μm. The particles are generally crystalline and substantially round, and when incorporated into the present formulation in an amount generally in the range of about 30 wt. % to about 90 wt. %, preferably in the range of about 40 wt. % to about 75 wt. %, provide a tablet having a porosity corresponding to a bulk density of at least 5.0 g/ml. A suitable product for this purpose is that obtainable commercially as Mannogem™ EZ from SPI Pharma Group and Pearlitol® 200 SD from Roquette Incorporated. PEARLITOL® 200 SD is a highly pure preparation of mannitol that can be used to generate tablets of high hardness at low or medium compression forces.

Diluents: Diluents, also termed fillers, are used to increase the bulk of a tablet, so that a practical size is provided for compression. Suitable diluents herein are those generally used in the art, and include, for example, dicalcium phosphate dihydrate (e.g., Di-Tab®, Stauffer), sugars that have been processed by cocrystallization with dextrin (e.g., co-crystallized sucrose and dextrin such as Di-Pak®, Amstar), calcium phosphate, cellulose, kaolin, mannitol, lactose, sorbitol, inositol, sodium chloride, dry starch, powdered sugar, and the like.

Lubricants and glidants: Lubricants are used in the field of pharmaceutical formulation typically during tablet manufacture, to prevent adhesion of the formulation and its components to the surfaces of the tableting equipment, e.g., punches and dies, and to reduce interparticle friction, facilitate removal of finished tablets, and to improve flow during granulation. The quantity of lubricant used is typically in the range of about 0.01 wt. % to about 5 wt. %, preferably in the range of about 0.01 wt. % to about 1.0 wt. %. Typical lubricants are stearates such as stearic acid, sodium stearyl fumarate, calcium stearate, zinc stearate, and magnesium stearate, a particularly common lubricant and useful herein. Other lubricants include hydrogenated vegetable oils, polyethylene glycol, liquid paraffin, and silicon dioxide. Glidants are useful herein when the formulation is prepared using a dry granulation or direct compression technique, to improve flow characteristics of a dry mixture. Colloidal silica (e.g., Cab-O-Sil®, Cabot) and talc are commonly used glidants and are useful in conjunction with the present invention. It should be noted that talc may serve as both a lubricant and a glidant.

Colorants: A colorant must be added if a colored formulation or dosage form is desired. Suitable colorants include natural colorants, i.e., pigments and dyes obtained from mineral, plant, and animal sources. Examples of natural colorants include red ferric oxide, yellow ferric oxide, annattenes, alizarin, indigo, rutin, and quercetin. Synthetic colorants may also be used, and will typically be an FD&C or D&C dye, e.g., an approved dye selected from the so-called "coal-tar" dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a "lake" thereof, i.e., an aluminum or calcium salt thereof. Particularly preferred colorants are food colorants in the "GRAS" (Generally Regarded As Safe) category. Particularly preferred colorants are also water soluble. In preparing the present formulations, colorant(s) are typically added to the pharmaceutical mixture prior to the granulating process. Since colorants can occasionally migrate during wet granulation and result in uneven coloring of the final dosage form, additives that mitigate against migration can be incorporated into the formulation e.g., tragacanth, acacia, talc, attapulgite, and the like. Migration of colorant during wet formulation can also be reduced by drying the granulation slowly at lower temperatures and stirring the granulation as it dries.

Sweeteners and flavoring agents: In order to enhance the taste of the dosage form, at least one sweetener is preferably incorporated into the formulation or dosage form. The sweetener may be a sugar, e.g., sucrose, fructose, or dextrose, or, more preferably, a non-sugar sweetening agent to reduce both caloric intake and the likelihood of dental caries. Sweeteners falling within the latter group include many well known artificial sweetening agents, such as, for instance, aspartame, saccharin, saccharin salts (e.g., sodium saccharin, calcium saccharin), sucralose, acesulfame potassium, neotame, sorbitol, xylitol, stevioside, steviol, mannitol, erythritol, lactitol, maltitol, alitame, neohesperitin dihydrochalcone, glucin, miraculin, monellin, and thaumatin. In lozenges of the invention, the sweetener is generally incorporated within the wet matrix, i.e., physically entrapped therein, while when the dosage form is a gum, this is not generally the case. Flavoring agents can be natural, artificial, or a combination thereof. Examples of suitable flavoring agents are flavor oils such as such as spearmint oil, peppermint oil, clove oil, cinnamon oil, citrus oils (e.g., lemon, lime, orange) and synthetic organics such as certain aldehydes and esters, e.g., cinnamyl acetate, cinnamaldehyde, citral diethylacetal, and the like. Flavorants may be used to provide for taste masking if one or more of the components render the formulation or dosage form bitter-tasting or otherwise unpleasant in taste, or may simply enhance a neutral flavor.

Coating: A tablet dosage form of the invention may be coated with one or more layers of membrane coating materials for sealing purposes, as is known in the art. An outer coating may also include one or more colorants to provide a colored dosage form as desired and/or to improve the taste of the tablet. These coatings may be sugar coatings, film coatings, color coatings, or the like.

The present formulations may also include a transmucosal absorption enhancer to facilitate permeation through the mucosal surfaces of the oral cavity. Such enhancers are known to those of skill in the art of pharmaceutical formulation, and/or are described in the pertinent texts and literature. Many such transmucosal absorption enhancers are gels. Specific examples of suitable transmucosal absorption enhancers include, without limitation, poloxamers, polyvinyl alcohol, polyethylene glycol, propylene glycol, fatty acid mono- and di-esters of glycerol (e.g., propylene glycol monolaurate), and fatty acid esters of polyethylene glycol (e.g., polyethylene glycol monolaurate).

The dosage forms herein, e.g., orally disintegrating tablets, can be of any suitable size and shape, and the invention is not limited in this regard. That is, the dosage forms may be, for instance, triangular, round, rectangular, square, biconvex, multilayered, or have an irregular shape. There may also be letters or characters embossed or printed on the dosage form surface.

The formulations of the invention can also be adapted for sublingual or buccal administration. In the former case, somewhat smaller and/or flatter dosage forms may be desirable, e.g., a thin film, or an orally disintegrable dosage form as otherwise provided herein may suffice without modifications made to size or shape. For buccal administration, the dosage form may be a tablet or film and will adhere to the oral mucosa, e.g., the gum, and, for that purpose, will contain at least one component that facilitates adhesion to the buccal mucosa until drug release and/or dosage form disintegration (which preferably occur roughly simultaneously) are complete. Such components are typically hydrophilic, water-swellable polymers that adhere to the wet surface of the buccal mucosa and include, for instance, e.g., carbomers, hydrolyzed polyvinylalcohol, polyethylene oxides, polyacrylates, and the like. For buccal administration the drug, or some portion thereof, diffuses through the oral mucosa and enters directly into the bloodstream. See, e.g., U.S. Pat. No. 6,284,262 to Place, U.S. Pat. Nos. 6,548,490, 7,927,623 and 8,613,950. Avanafil is a BCS-2B drug, characterized by high permeability, relatively poor solubility at neutral and high pH and good solubility at low pH, making it suitable for buccal delivery.

Dissolvable oral thin films (OTFs) may be used for delivery of avanafil. Dissolvable films are often composed of an aqueous polymer matrix. Dissolvable film employed in buccal systems may be designed as bioerodable mono- or multi-layers systems and may feature a mucoadhesive tailored for the desired dwell time. Bioerodible systems offer patients the convenience of rapid onset and complete system disintegration. The size of the film may be, for example, about 4 to 10 cm$^2$ with a depth of 0.1 to 4 mm. The dimensions of the film will be proportionate to the dose of the active agent, e.g. larger doses requiring larger films.

In another aspect, avanafil is provided in an oral formulation using amorphous dispersions that may be made by hot-melt extrusion involving co-melting of the drug substance and an appropriate polymeric excipient. The active agent may also be micronized or formed into nanocrystals prior to incorporation into a film, gel or tablet dosage form.

In addition, the formulations and dosage forms herein may be made effervescent using components and techniques known to those of ordinary skill in the art and/or described in the pertinent texts and literature. See, e.g., Remington: The Science and Practice of Pharmacy, Nineteenth Edition, cited previously. For example, prior to compaction, and preferably during the initial phase of formulation, sodium bicarbonate and either citric acid, tartaric acid, or sodium bisphosphate are blended into the mixture so as to become incorporated into the final product. On contact with water, i.e., in the oral cavity, carbon dioxide is released as a result of the acid-base reaction that occurs; the effervescence serves to at least partially taste mask any unpleasant taste associated with one or more components in the dosage form or formulation, e.g., that of the active agent itself.

Taste masking may also be accomplished in other ways, as noted above, e.g., using sweeteners and flavoring agents as described above, other flavoring agents, or by coating the dosage form with one or more coatings effective to provide taste masking, as is known in the art.

Methods of Use:

The formulations and dosage forms of the invention may be used to treat any adverse condition, disease or disorder that are generally treatable with a Type V phosphodiesterase inhibitor (PDE V inhibitor). The pharmacological and physiological mechanisms and effects of PDE V inhibitors suggest the utility of these agents in treating a variety of conditions, diseases and disorders in which modulation of smooth muscle, renal, hemostatic, inflammatory, and/or endocrine function is desirable. Adverse conditions, diseases, and disorders treatable by PDE V inhibitors and thus treatable using the formulations and dosage forms of the invention include, but are not limited to, erectile dysfunction, premature ejaculation, female sexual dysfunction, cardiovascular, cerebral stroke, congestive heart failure, cerebrovascular conditions, ischemic heart disease, pulmonary arterial hypertension, acute respiratory distress syndrome, benign prostatic hypertrophy, atherosclerosis, autoimmune diseases, overactive bladder, bladder outlet obstruction, incontinence, cachexia, cancer, diabetes, endarterectomy, diseases characterized by disorders of gut motility, dysmenorrhoea, elevated intraocular pressure, glaucoma, glomerular renal insufficiency, hyperglycemia, hypertension, impaired glucose tolerance, inflammatory diseases, insulin resistance syndrome, intestinal motility, macular degeneration, nephritis, optic neuropathy, osteoporosis, peripheral arterial disease, polycystic ovarian syndrome, renal failure, respiratory tract disorders, thrombocytemia, tubular interstitial diseases, and urologic disorders. Urological disorders include female and male sexual dysfunctions.

Allergic disorders include, but are not limited to, urticaria, eczema, and rhinitis.

Cardiovascular diseases include, but are not limited to, atherosclerosis, restenosis, hypertension, acute coronary syndrome, angina pectoris, arrhythmia, a cardiovascular disease associated with hormone replacement therapy, cerebral infarction, cerebral ischemia, conditions of reduced blood vessel patency (e.g., postpercutaneous transluminal coronary or carotid angioplasty, or post-bypass surgery graft stenosis), deep vein thrombosis, disseminated intravascular coagulation syndrome, heart disease, heart failure, migraine, myocardial infarction, peripheral vascular disease, Raynaud's disease, renal ischemia, renal vascular homeostasis, thrombotic or thromboembolytic stroke, venous thromboembolism, pulmonary arterial hypertension, congestive heart failure, myocardial infarction and angina, and prevention of any such cardiovascular condition or event subsequent to a first cardiovascular event (i.e., "secondary prevention").

Diseases characterized by disorders of gut motility include, but are not limited to, irritable bowel syndrome, diabetic gastroparesis and dyspepsia.

Female sexual dysfunction (FSD) includes, but is not limited to, clitoral dysfunction, female hypoactive sexual desire disorder, female sexual arousal disorder (FSAD), female sexual pain disorder, and female sexual orgasmic dysfunction (FSOD).

Respiratory tract disorders include, but are not limited to, acute respiratory failure, allergic asthma, allergic rhinitis, bronchitis, chronic asthma, reversible airway obstruction, and allergic disorders associated with atopy (such as urticaria, eczema, or rhinitis).

Other medical conditions for which a PDE V inhibitor is indicated, and for which treatment with the formulations of the present invention may be useful include, but are not limited to, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g., gastroparesis, peripheral diabetic neuropathy), Alzheimer's disease, psoriasis, skin necrosis, metastasis, baldness, nutcracker oesophagus, anal fissure, hemorrhoids, insulin resistance syndrome, hypoxic vasoconstriction as well as the stabilization of blood pressure during hemodialysis.

Preferably, the diseases treated using the formulations of the invention include erectile dysfunction, pulmonary arterial hypertension, congestive heart failure, benign prostatic hypertrophy, myocardial infarction and angina.

Often, the formulations and dosage forms of the invention will be prescribed for and used in the prevention and treatment of erectile dysfunction. As explained in U.S. Pat. No. 6,403,597 to Wilson et al., rapid release dosage forms such as those provided herein are uniquely suited to as-needed administration prior to sexual activity.

Avanafil may be provided in a daily dose ranging from 10 mg to 800 mg. Exemplary doses may be 50 mg, 100 mg or 200 mg. For most patients a starting dose of 100 mg may be taken 15 to 30 minutes before sexual activity on an as needed basis. Avanafil taken in tablet form is rapidly absorbed after oral administration, with a median Tmax of 30 to 45 minutes in the fasted state. When 100 mg or 200 mg is taken with a high fat meal, the rate of absorption is reduced, with a mean delay in Tmax of 1.12 to 1.25 hours and a mean reduction in Cmax of 24% (100 mg) and 39% (200 mg). There was an approximate 3.8% decrease in AUC. The small changes in avanafil Cmax and AUC are considered of minimal clinical significance; therefore, avanfil may be administered with or without food. Avanafil is cleared predominantly by hepatic metabolism, mainly by the CYP3A4 enzyme and to a minor extent by CYP2C isoform. The plasma concentrations of the major circulating metabolites, M4 and M16, are approximately 23% and 29% that of the parent compound, respectively. The M4 metabolite has an in vitro inhibitory potency for PDE5 18% of that of avanafil and M4 accounts for approximately 4% of the pharmacologic activity of avanafil. The M16 metabolite was inactive against PDE5.

Method of Manufacture:

Formulations and dosage forms of the invention may be prepared using conventional techniques used in the fabrication of oral drug preparations, e.g., direct compression, roller compaction, dry granulation, or wet granulation. In one aspect of the invention, a new and particularly effective technique is provided for preparing the preferred rapidly disintegrating oral avanafil dosage forms described herein, such that absorption is increased despite the fact that avanafil and its analogs are poorly soluble at the typical pH of the duodenum. The new technique may employ any of the aforementioned dosage form preparation methods, i.e., direct compression, dry granulation, or wet granulation. The novel method of manufacturing, while an optimal process for formulating the dosage forms described and claimed herein, may be used to manufacture orally disintegrating tablets in general, i.e., with other active agents and the like, and may not always employ an absorption enhancing composition.

In direct compression and roller compaction, the particulate material to be included in the dosage form is compressed in a tablet press or subjected to compaction in a roller mill directly. Dry granulation, as is known in the art, may be utilized effectively when at least one of the formulation components has sufficient cohesive properties to be tableted. Wet granulation involves mixing the components that will comprise the dosage form in a blender, e.g., a twin shell blender or a double-cone blender, and thereafter adding solutions of additional component(s), including at least one binding agent, to obtain a granulation. The damp mass is then screened using a sieve with pre-defined mesh sizes followed by drying with a fluid bed dryer, a spray dryer, vacuum, or the like. Additional information and details concerning these processes are described at length in the pertinent texts and literature, and will in any case be known to those of ordinary skill in the art of pharmaceutical formulation.

The manufacturing method of the invention involves a multi-step process in which the mixture of components that will be incorporated into the final oral dosage form is divided and separately processed. In particular, the method involves: an initial step in which a fraction, i.e., some but not all, of the formulation used to prepare the dosage form, is mixed, process in a manner to provide particles or granules, and dried; a second step in which the remainder of the formulation is blended in; and, finally, compaction of the entire mixture using a tablet press or other compression technique, to prepare the rapidly disintegrating oral dosage form. Generally, the first two steps involve dry or wet granulation, although, as noted, other techniques may be used. Preferably, the first fraction of the formulation contains active agent, a disintegrant, e.g., a superdisintegrant, a porous binder, and optionally one or more additional binders, such that the initial step of the process provides active agent granules, while the remainder of the formulation that is later blended in contains a lubricant, additional disintegrant, and additional porous binder. The steps, i.e., the initial step as well as the second step, are, as noted, preferably granulation steps, and most preferably are carried out using wet granulation techniques and equipment.

In a preferred embodiment, all of the active agent is subject to granulation in the initial step of the process, such that prior to the second step, active agent granules are prepared and dried. When an absorption enhancing composition is employed, it is preferred that all of that composition is incorporated in the initial step as well, such that the active agent and absorption enhancing composition are intimately admixed prior to further processing. It is also preferred that any lubricant be added in only the second step, while the porous binder be added in only the second step or in both steps. Dividing the total amount of porous binder in this way reduces the likelihood that the component will collapse and lose its ability to dissolve quickly, as can happen with porous superdisintegrants that can serve as binders in rapidly disintegrating dosage forms. The porous binder, e.g., porous mannitol, may be divided in an approximately 50-50 manner, although generally the ratio of porous binder incorporated in the initial step to the porous binder in the second step may be anywhere from about 5:1 to 1:5, preferably 3:1 to 1:3, and most preferably 2:1 to 1:2.

The relative amounts of the components in the composition is as follows, based on the percentage by weight of the final dried dosage form: active agent, about 10% to about 50%; porous binder/superdisintegrant (e.g., a directly compressible carbohydrate such as porous mannitol), about 30% to about 85%, preferably about 40% to about 75%; lubricant, about 0.01% to about 3.0%, preferably in the range of about 0.01% to about 1.0%; other components such as colorants, sweeteners, flavoring agents, etc., 0% to about 5%, preferably 0.1% to about 5%. When an absorption enhancing composition is used, the active agent and absorption enhancing composition will generally although not necessarily together represent about 10 wt. % to 70 wt. % of the final dosage form, with the active agent and absorption enhancing composition generally in a ratio in the range of about 10:1 to about 1:5.

Manufacturing the formulations and dosage forms of the invention in this way significantly enhances the competing physical properties most desired in a rapidly disintegrating tablet: on the one hand, physical integrity, as represented by the tablets' hardness, in turn enabled by achieving a high bulk density; and, on the other hand, rapid disintegration time, because of the significant amount of porous binder that can be incorporated in the multi-step method. For instance, using the above-mentioned technique, oral dosage forms can be prepared which disintegrate within the oral cavity within about 45 seconds and exhibit a hardness of greater than about 30 N. Preferred oral dosage forms herein disintegrate within the oral cavity within about 30 seconds and exhibit a hardness of greater than about 15 N, and most preferred oral dosage forms prepared using the present method disintegrate within the oral cavity within about 15 seconds and exhibit a hardness of greater than about 7.5 N.

Method for Selecting Compositions to Enhance Duodenal Absorption:

The invention also provides a method for evaluating and selecting a compound or combination of compounds that will enhance the absorption of avanafil in the duodenum by reducing precipitation and/or aggregation of the active agent upon leaving the stomach and entering the higher pH environment of the duodenum. The method used involves a photometric analysis in which the amount of light transmitted by a composition containing the active agent and a candidate composition is measured as a function of time, with decreasing transmission indicative of precipitation and/or aggregation. Selection criteria involve factors such as aggregation onset time, transmission lowering rate, and asymptotic transmission.

The photometric method is carried out as follows. A known quantity of a candidate compound or composition, i.e., a compound or composition undergoing evaluation as a potential absorption enhancing composition herein, is dissolved in water that has been acidified to a pH of about 2.5, thereby approximating the pH of the stomach. After dissolution is complete, as may be monitored visually, the pH of the solution is increased to about 7.0, to approximate the pH of the duodenum. This may be done with any suitable basifying agent. As soon as a pH of 7.0 is reached, a source of light (e.g., an HeNe laser) is turned on and directed into the solution, and transmission measurements are made at regular time intervals, e.g., every ten seconds, every twenty seconds, every thirty seconds, etc., up to at least thirty minutes. Normalized transmission values—i.e., the fraction of the transmission seen at time "zero," when the active agent is in solution—is evaluated at each time point, and the results plotted, as done in Example 2. Results are compared with a control experiment using only the active agent without any candidate component or composition present.

A candidate compound or composition was determined to "reduce the precipitation and/or aggregation" of avanafil upon titration of the solution to pH 7.0 if the compound was found to (1) delay the onset of avanafil precipitation at pH 7.0, (2) prolong the time period during which avanafil precipitates following titration of the avanafil solution to 7.0, (3) delay the start of the process in which precipitated avanafil is visually observed to form aggregates, or (4) prolong the time period during which precipitated avanafil was observed to form aggregates. Among many successful such candidates and compounds are the poloxamers, i.e., polyoxyethylene-polyoxypropylene block copolymers, as described in detail earlier herein.

It is to be understood that while the invention has been described in conjunction with the preferred specific embodiments thereof that the foregoing description as well as the examples that follow are intended to illustrate and not limit the scope of the invention.

EXAMPLE 1

A high performance liquid chromatography (HPLC) procedure was used to evaluate the aqueous solubility of avanafil (obtained from Tanabe Seiyaku Co., LTD, purity, 97.0% to 103% with an observed purity of 98.89%; particle diameter, 10-20 microns with median observed particle diameter of 18.47 microns) at a range of pH values. The HPLC conditions were as follows: system, HP Model 1100; analytical column, Supelco Kromasil C8, 4.6 mm×250 mm, 5 μm particle size; assay injection volume, 20 μl; stock stability injection volume, 0.5 μl; needle wash volume, 91 μl; mobile phase flow rate, 1.00 ml/minute; column temperature, 30° C.; detection wavelength 246 nm; flow cell path length, 10 mm; range step 2.00 nm; threshold, 1.00 mAU; stop time, 30 minutes. The results are presented in Table 1. Solutions 1, 2, 3, 6, 7, 8, 11, and 12 were buffered to pH values of 0.99, 2.00, 3.00, 6.00, 7.00, 8.00, 11.0, and 12.0, respectively, using a phosphate buffer, 0.1M KH$_2$PO$_4$. Solutions 4 and 5 were buffered to pH values of 4.00 and 5.00, respectively, using a sodium acetate buffer, 0.1M NaOAc, while solutions 9 and 10 were respectively buffered to pH values of 9.00 and 10.00 using a sodium carbonate buffer, 0.1M Na$_2$CO$_3$.

TABLE 1

| Solution | Buffer | Solution pH | Solubility, μl/ml |
| --- | --- | --- | --- |
| ASTM Type II H$_2$O | None | — | 0.139 |
| Solution 1 | 0.1M KH$_2$PO$_4$ | 0.999 | >199,000 |
| Solution 2 | 0.1M KH$_2$PO$_4$ | 2.00 | 35,000 |
| Solution 3 | 0.1M KH$_2$PO$_4$ | 3.00 | 1,700 |
| Solution 4 | 0.1M NaOAc | 4.00 | 344 |
| Solution 5 | 0.1M NaOAc | 5.00 | 19.5 |
| Solution 6 | 0.1M KH$_2$PO$_4$ | 6.00 | 1.28 |
| Solution 7 | 0.1M KH$_2$PO$_4$ | 7.00 | 0.233 |
| Solution 8 | 0.1M KH$_2$PO$_4$ | 8.00 | 0.0520 |
| Solution 9 | 0.1M Na$_2$CO$_3$ | 9.00 | <0.0500 |
| Solution 10 | 0.1N Na$_2$CO$_3$ | 10.0 | <0.0500 |

TABLE 1-continued

| Solution | Buffer | Solution pH | Solubility, μl/ml |
| --- | --- | --- | --- |
| Solution 11 | 0.1M KH$_2$PO$_4$ | 11.0 | 0.0568 |
| Solution 12 | 0.1M KH$_2$PO$_4$ | 12.0 | <0.0500 |

As expected, the solubility of avanafil markedly decreased with increasing pH, evidencing solubilities of 35,000 μl/ml at a pH of 2.00, 1,700 μl/ml at a pH of 3.00, and 0.233 μl/ml at a pH of 7.00. The latter value represents the solubility of avanafil at the approximate pH of the duodenum, while the solubility of avanafil in the stomach will normally fall between the first two values, as the pH in the average stomach is approximately 2.5.

EXAMPLE 2

Various compounds were evaluated for their ability to increase the aqueous solubility of avanafil at an elevated pH by reducing the precipitation and/or aggregation of avanafil following titration of an aqueous solution of avanafil at pH 2.5 to a pH of 7.0, as follows.

Avanafil, 33.3 mg, and 13.3 mg of the compound(s) to be evaluated were weighed out and added to 300 ml of DI water in a beaker. Mixing was carried out using a magnetic stirrer at low speed, approximately 50 rpm to 100 rpm. Hydrochloric acid, 0.2M, was gradually added until a pH of 2.5 was reached; this pH was selected as the starting point for the evaluation since it is the average pH of the stomach. Mixing was continued for a short time to ensure dissolution of the avanafil and the compound(s) being evaluated.

Then, sodium hydroxide was gradually added to raise the pH to approximately 7.0, the average pH of the duodenum. As soon as a pH of 7.0 was reached, an HeNe laser was turned on and transmitted into the solution in the beaker. The transmission as a function of time was measured and photographs of the solution were taken at regular intervals, until the transmission was lowered by at least a factor of ten. At this point, the laser was turned off and the solution was allowed to sit for at least 30 minutes, to observe the end state of the experiment. Turbidity was also determined, by evaluating the difference between the scattered light and the transmitted light at each measurement interval.

Each compound evaluated was determined to be a promising candidate for incorporation into an avanafil ODT if the compound increased the solubility of avanafil at pH 7.0, as determined from the optical measurement(s) made at the 30-minute point, and/or reduced the precipitation and/or aggregation of avanafil following titration of the aqueous avanafil solution from pH 2.5 to a pH of 7.0. A compound was determined to "reduce the precipitation and/or aggregation" of avanafil upon titration of the solution to pH 7.0 if the compound was found to (1) delay the onset of avanafil precipitation at pH 7.0, (2) prolong the time period during which avanafil precipitates following titration of the avanafil solution to 7.0, (3) delay the start of the process in which precipitated avanafil is visually observed to form aggregates, or (4) prolong the time period during which precipitated avanafil was observed to form aggregates.

A control experiment was also run using 46.6 mg avanafil in 300 ml DI water without any additional compounds present.

The compounds evaluated using the aforementioned procedures were as follows: Fumaric acid; Polyvinyl alcohol (PVA); Tween 20; Tween 80; Tween 80/Span 20 in a 6:4 wt. ratio; Tween 80/Span 20 in a 6:4 wt ratio with PVA; Tween 80/ascorbic acid mixture; Sodium dodecyl sulfate (SDS); Poloxamer 188; Poloxamer 407; TPGS; Polyethylene glycol 200; Polyethylene glycol 400; Polyethylene glycol 600; Polyethylene glycol 1000; Polyethylene glycol 3500; Sodium lauryl sulfate (SLS); Stearyl alcohol; Steric acid; Sodium acetate; Sucrose palmitate (SE D-1616, Mitsubishi); and Sucrose stearate (SE D-1815, Mitsubishi).

Figure 2:
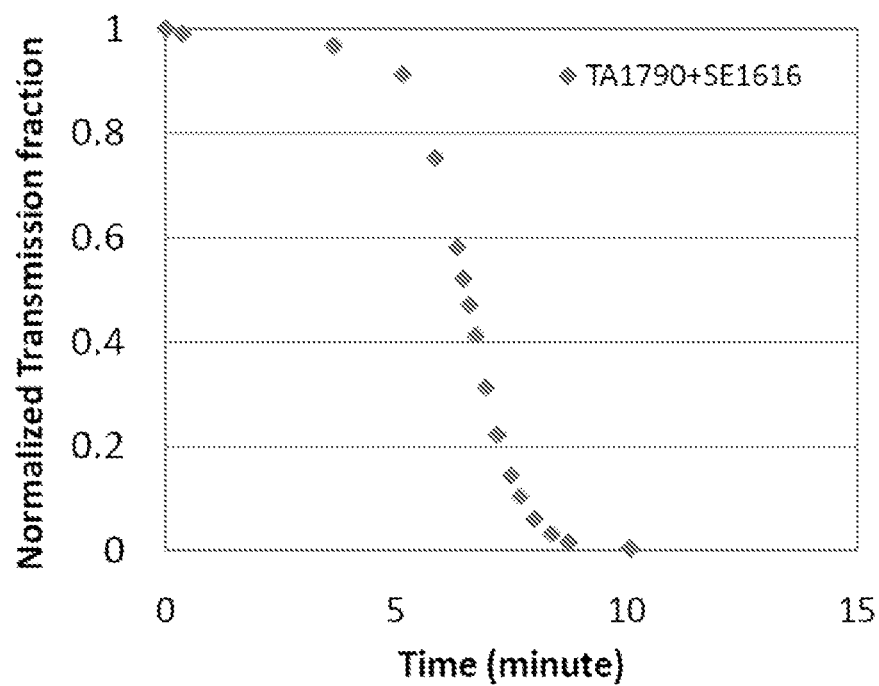
FIG. 2 is a graph of normalized transmission fraction versus time for the experiment conducted using sucrose palmitate, as described in Example 2.
Figure 3:
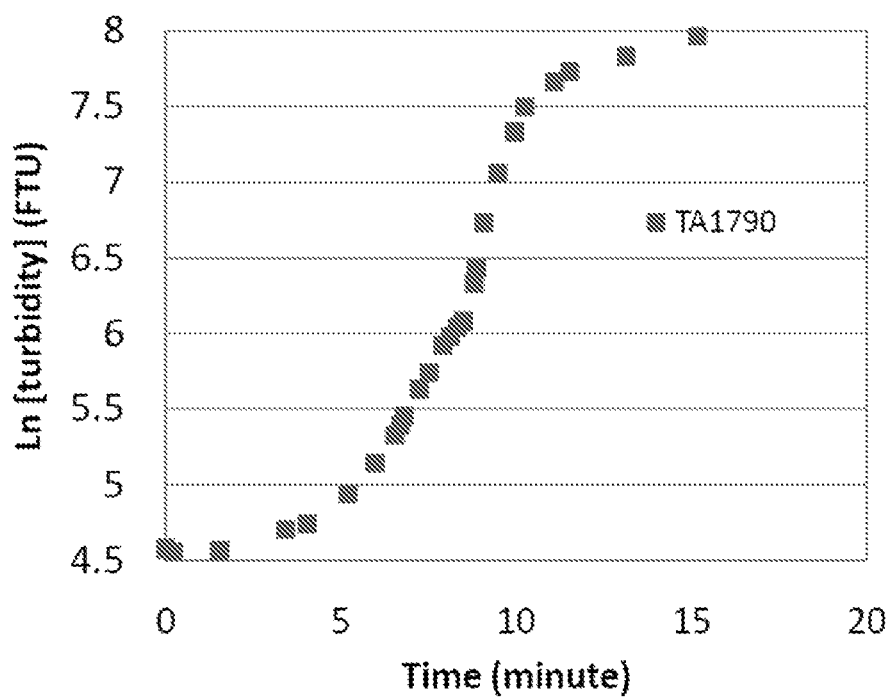
FIG. 3 is a graph indicating the turbidity (FTU) measurements made over time for the control experiment described in Example 2.
Figure 4:
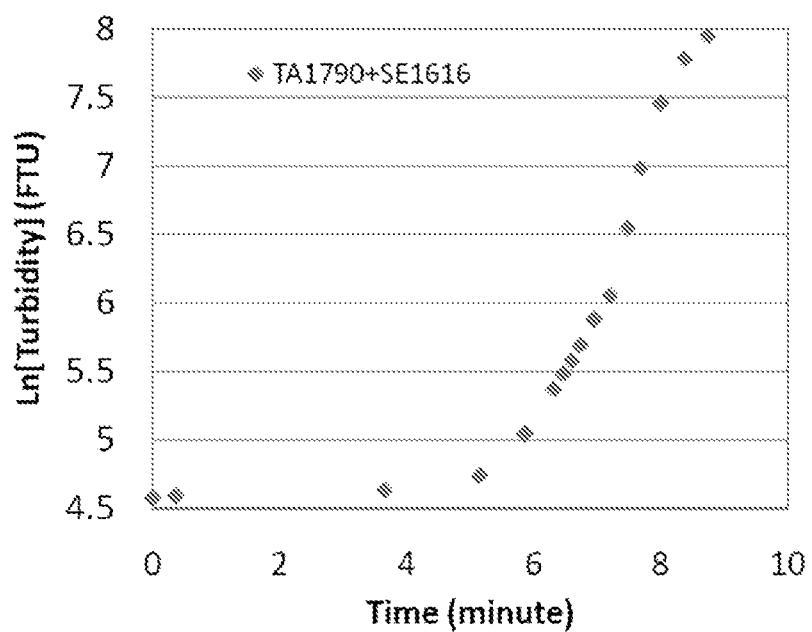
FIG. 4 is a graph indicating the turbidity (FTU) measurements made over time for the experiment conducted using sucrose palmitate, as described in Example 2.

For each of these candidate compound(s), normalized transmission fraction (i.e., measured transmission as a fraction of an initial transmission set equal to 1.0) was plotted versus time. The results for the control solution, containing avanafil without an added candidate compound are shown in FIG. 1 and the results for sucrose palmitate, SE1616, are shown in FIG. 2. Turbidity (FTU) measurements that were made are plotted in FIG. 3 for the control and in FIG. 4 for sucrose palmitate.

EXAMPLE 3

A tablet containing about 50% avanafil was made using a method that included a first mixing step where approximately half the total amount of PVP and magnesium stearate was added prior to granulation and the remaining PVP and magnesium stearate was added after granulation.

| Ingredient | Composition (%) |
| --- | --- |
| Avanafil (Lot: 17AP303020) | 50.02 |
| Pearlitol 200 SD (Roquette, Lot: E233P) | 37.13 |
| XL-10 PVP (ISP, lot: 3600163932) | 3.94 |
| Pepper Mint (Adams Extract, exp: 6 Sep. 2009) | 6.19 |
| Ascorbic acid (Science Lab: Lot: SLA1972) | 0.22 |
| Magnesium Stearate dihydrus (Tyco-Mallinkrodt; Lot: J03970) | 2.09 |
| Color-LB-1587 Green (Colorcon Lot TS 045675) | 0.27 |
| Ace K (Premium ingredients international; Lot: 20080131) | 0.13 |
| Neotame (NutraSweet Company; Lot: B604066256) | 0.01 |

Process: Mix 50% of the ISP PVP XL-10 with all other ingredients except Magnesium Stearate dihydrus at room temperature. Roller compact the mixture. Granulate the compacted ribbons by passing through Mesh 20 sieving screen. Add the remaining 50% of PVP XL-10 and Magnesium Stearate dihydrus to the screened granules. Tablet press and measure hardness (13.5N). Measure disintegration time (oral test: 7 seconds).

EXAMPLE 4

A tablet containing about 34% avanafil was made using a method that included a first mixing step where approximately half the total amount of PVP and magnesium stearate was added prior to granulation and the remaining PVP and magnesium stearate was added after granulation.

| Ingredient | Composition (%) |
| --- | --- |
| Avanafil (Lot: 17AP303020) | 34.30 |
| Pearlitol 200 SD (Roquette, Lot: E233P) | 48.90 |
| XL-10 PVP (ISP, lot: 3600163932) | 5.21 |
| Pepper Mint (Adams Extract, exp: 6 Sep. 2009) | 8.15 |
| Ascorbic acid (Science Lab: Lot: SLA1972) | 0.19 |
| Magnesium Stearate dihydrus (Tyco-Mallinkrodt; Lot: J03970) | 2.72 |
| Color-LB-1587 Green (Colorcon Lot TS 045675) | 0.34 |
| Ace K (Premium ingredients international; Lot: 20080131) | 0.17 |
| Neotame (NutraSweet Company; Lot: B604066256) | 0.02 |

Process: Mix 50% of the ISP PVP XL-10 with all other ingredients except Magnesium Stearate dihydrus at room temperature. Roller compact the mixture. Granulate the compacted ribbons by passing through Mesh 20 sieving screen. Add the remaining 50% of PVP XL-10 and Magnesium Stearate dihydrus to the screened granules. Tablet press and measure hardness (19.7N). Measure disintegration time (oral test: 16 seconds).

EXAMPLE 5

Formulation with fumaric acid.

| Ingredient | Composition (%) |
| --- | --- |
| Avanafil (Lot: 17AP303020) | 40.40 |
| Pearlitol 200 SD (Roquette, Lot: E233P) | 50.50 |
| Fumaric Acid | 1.80 |
| XL-10 PVP (ISP, lot: 3600163932) | 4.50 |
| Magnesium Stearate dihydrus (Tyco-Mallinkrodt; Lot: J03970) | 2.50 |
| Ace K (Premium ingredients international; Lot: 20080131) | 0.30 |

Process: Weigh 4 gm avanafil in a jar. Weigh 5 gm of Pearlitol 200 SD in a separate jar. Add 1.8 gm of fumaric acid solution (pH=1.98) to the avanafil jar and mix well. When avanafil is fully mixed, add the 5 gm of Pearlitol 200 SD from the other jar to the avanafil/fumaric acid jar and mix well. Add Ace K. Wet granulate through a mesh=18 curved screen and dry at 65° C. for 1 hr. Add magnesium stearate and X1-10 PVP. Check bulk density, flowability; add lubricant if necessary. Tablet press and check hardness (40-60 N) and friability (<1%). Measure disintegration time (USP 701: 25 seconds; oral test: 12 seconds).

EXAMPLE6

Formulation with added surfactant. As an example of a formulation where a surfactant was added to improve solubility at neutral pH, Tween 80/Span 20 was used.

| Ingredient | Composition (%) |
| --- | --- |
| Avanafil (Lot: 17AP303020) | 34.13% |
| Pearlitol 200 SD (Roquette, Lot: E233P) | 42.68% |
| X-10 PVP (ISP, lot: 3600163932) | 4.88% |

-continued

| Ingredient | Composition (%) |
|---|---|
| Magnesium Stearate dihydrate (Tyco-Mallinkrodt; Lot: J03970) | 7.74% |
| Tween 80/Span 20 (6:4) | 8.53% |
| Ace K (Premium ingredients international; Lot: 20080131) | 2.04% |

Process: Weigh 4 gm avanafil in a jar. Add 0.6 gm of Tween 80/Span 20 (6:4) to the Avanafil jar. Then add 0.7 ml deionized water to the jar. Wet granulate the mixture and pass through a 30 mesh screen, then dry in ambient temperature overnight. Sieve through the 30 mesh screen again and check bulk density and flowability. Add Pearlitol 200 SD and Ace K. Tablet press and measure hardness (40-60 N) and disintegration time (oral: 15 seconds).

We claim:

1. An orally disintegrating tablet, consisting of the following:
   a therapeutically effective amount of avanafil;
   an absorption enhancing composition comprising a surfactant;
   an orally disintegrating composition comprising a disintegrant; and
   a porous component in a pharmaceutically acceptable carrier,
   wherein the surfactant comprises a polymeric component that mitigates the precipitation of avanafil in an aqueous medium as pH increases from about 2.5 to about 7.0.

2. The tablet according to claim 1, wherein the tablet disintegrates within the oral cavity within about 45 seconds and exhibits a hardness of greater than about 30 N.

3. The tablet according to claim 2, wherein the tablet disintegrates within the oral cavity within about 30 seconds and exhibits a hardness of greater than about 15 N.

4. The tablet according to claim 2, wherein the tablet disintegrates within the oral cavity within about 15 seconds and exhibits a hardness of greater than about 7.5 N.

5. The tablet according to claim 1, wherein the disintegrant is a superdisintegrant.

6. The tablet according to claim 1, wherein the porous component comprises porous mannitol.

7. The tablet according to claim 1, wherein the polymeric component is nonionic and mitigates the precipitation of avanafil in an aqueous medium as pH increases from about 2.5 to about 7.0 by delaying precipitation, reducing the rate of precipitation, decreasing the extent of precipitation, or any combination of the foregoing.

8. The tablet of claim 7, wherein the polymeric component is comprised of a hydrophilic segment and a hydrophobic segment.

9. The tablet according to claim 7, wherein the polymeric component is comprised of a polyoxyethylene-polyoxypropylene copolymer.

10. The tablet according to claim 9, wherein the polymeric component comprises poloxamer 407.

11. The tablet according to claim 1, wherein the avanafil represents in the range of about 10 wt. % to about 50 wt. % of the tablet.

12. The tablet according to claim 11, wherein the avanafil represents up to about 70 wt. % of the dosage form.

13. An orally disintegrating tablet according to claim 1, having hardness of 13.5 N or more, which is obtained by a process comprising the following steps:
   preparing active agent granules by (i) blending avanafil in particulate form with a first fraction of a disintegrant and a first fraction of a porous binder, to form an initial mixture, and (ii) granulating the initial mixture for a predetermined time period at a predetermined temperature, to provide the active agent granules, wherein granulating is carried out in a solvent; drying the active agent granules;
   blending the dry active agent granules with a lubricant, a second fraction of the disintegrant, and a second fraction of a porous binder, to provide a final formulation mixture; and
   compacting the final formulation mixture to prepare the orally disintegrating tablet, wherein the tablet does not comprise fumaric acid, tartaric acid, succinic acid, malic acid, ascorbic acid or aspartic acid.

* * * * *